United States Patent [19]

Sweet

[11] Patent Number: 4,548,080
[45] Date of Patent: Oct. 22, 1985

[54] METHOD AND APPARATUS FOR SOIL MECHANICS MEASUREMENTS OF FILTER CAKES

[75] Inventor: Edmund G. F. Sweet, Burlington, Canada

[73] Assignee: Ontario Research Foundation, Ontario, Canada

[21] Appl. No.: 594,116

[22] Filed: Mar. 28, 1984

[51] Int. Cl.⁴ .............................................. E21B 49/10
[52] U.S. Cl. ................................. 73/432 SD; 73/61.4; 73/151
[58] Field of Search .................. 73/73, 432 SD, 61.4, 73/153, 151; 166/255; 175/40

[56] References Cited

U.S. PATENT DOCUMENTS 2,830,266  4/1958  Southwick et al. .................. 73/61.4
4,458,528  7/1974  Roper et al. .......................... 73/151

Primary Examiner—Stewart J. Levy
Assistant Examiner—Hezron E. Williams
Attorney, Agent, or Firm—Sim & McBurney

[57] ABSTRACT

An apparatus includes a main housing with a permeable cylindrical sleeve in the main housing to simulate a rock formation through which a well is drilled. A compartment is defined outside the sleeve and a solids-containing fluid is introduced into the interior of the sleeve and pressurized, so that the fluid passes through the sleeve and into the compartment, leaving a filter cake on the inside of the sleeve. A probe extends through the sleeve to simulate a drill string, and the probe can be moved toward and away from the inside surface of the sleeve. The apparatus includes a means for determining the filter cake thickness, preferably ultrasonically.

33 Claims, 5 Drawing Figures

METHOD AND APPARATUS FOR SOIL MECHANICS MEASUREMENTS OF FILTER CAKES

This invention relates generally to a method and apparatus for making particular measurements on a filter cake within an apparatus intended to simulate down-hole conditions in a drilled well. More particularly, the invention has to do with improvements and additions to an apparatus described in co-pending U.S. patent application Ser. No. 551,343, filed on Nov. 14, 1983, entitled, "BORE-HOLE HYDRAULICS SIMULATOR", the latter invention being adapted to bring about the deposition of a filter cake on a permeable, cylindrical sleeve simulating a rock formation through which a well is drilled, the filter cake resulting from deposition of the solid phase while the fluid phase passes through the permeable sleeve, as the fluid is driven to move from a high pressure area within the sleeve to a lower pressure area in a compartment exterior to the sleeve.

Even more particularly, this invention relates to a method and apparatus adapted to determine soil mechanics properties of a drilling fluid filter cake, and additionally has the ability to bring about asymmetric flow of the fluid thus likely giving rise to a filter cake of varying thickness. The apparatus has additionally the capability of determining the thickness profile of such a filter cake.

BACKGROUND OF THIS INVENTION

As is well known, drilling fluid is utilized in well-drilling operations for a number of basic purposes. One purpose is to cool and lubricate the bit and the string. Another is to carry up to the surface the bore hole material which is produced as a result of the drilling operation. A third purpose is to deposit a tough and low-permeability filter cake against the sides of the bore-hole and thus reduce the invasion of the fluids phase into the formation and control fluid losses down hole. A fourth is to overbalance formation pore-pressures with sufficient hydrostatic head in order to control well flowing. A fifth is for control of corrosion of the drill string and bit. A sixth is to buoyantly support the drill string.

Due to geothermal heat in the surrounding formations, the temperature of the drilling fluid can rise as high as 600° F. or more. The pressure of the drilling fluid is a function of depth and density. For very deep wells, the pressure of the drilling fluid at the bottom of the well can be as high as 20,000 psi or more.

It is very important for the drilling fluid not only to deposit a low permeability filter cake on the borehole wall, but one which is sufficiently tough and cohesive to resist erosion by the upwardly flowing drilling fluid in contact with the borehole walls.

The co-pending U.S. application Ser. No. 551,343, filed Nov. 14, 1983, is directed to an apparatus which comprises a main housing, a permeable cylindrical sleeve fixed with respect to the main housing and simulating a rock formation through which a well is drilled, first means defining a compartment exterior to the sleeve, second means for introducing into the interior of the sleeve a solids-containing fluid and for raising the fluid to a pressure higher than the pressure in the compartment, whereby the fluid passes through the sleeve and into the compartment, leaving a filter cake on the inside of the sleeve, and a probe extending through the sleeve and simulating a drill string. The apparatus is capable of depositing a filter cake and of making various measurements under controlled hydraulic regimes.

The present invention pertains to an apparatus for cooperation with the apparatus just described, which allows a determination of the soil mechanics properties of the filter cake, and the profile of filter cake thickness measured circumferentially around the sleeve. The apparatus is also capable of off-centering the probe, which may induce non-uniform filter cake thickness.

In a general way, it is important to be able to determine the effect of various hydraulic regimes on a filter cake in relation to its soil mechanics properties.

As used hereinafter the word "stickometry" will refer to the laboratory measurement of the force required to break a contact probe free of a filter cake, thus modelling a possible down-hole condition. This deserves further explanation.

As used hereinafter, the word "consolidometry" will refer to the rate and degree of consolidation of the filter cake.

When drilling a well, the drill string normally does not remain in an axially centred position with respect to the hole being drilled. Often, the hole will deviate, and the drill string will tend to approach the side of the drill hole. As previously stated, when the fluid phase of the drilling fluid seeps away into surrounding rock strata where the same is permeable, a filter cake of lower permeability is deposited on the sides of the hole, thus cutting down on the loss of fluid. However, in the event that the drill string is stopped when in contact with the filter cake, it will be appreciated that the drill string develops differential pressure sticking because the filter cake masks a portion of the drill string from a balanced hydrostatic condition. The force resulting from this differential pressure sticking can be substantial.

At present, several methods are utilized to try to break the drill string free of its stuck position against the filter cake. One of these is simply to cause a shock load in the drill string, while rotational torque is applied. Another is to introduce a lubricant, called a spotting fluid, into the zone of sticking within the bore hole. The intent of the spotting fluid is to consolidate the filter cake and provide lubrication. The drill string is then worked or cyclically loaded, in an attempt to break the sticking contact.

It would be extremely useful to be able to determine the stickometric properties of various filter cakes, in order to allow an optimization of formulation and technique to reduce the differential pressure sticking effect.

The consolidometric nature of the filter cake is also useful to know when comparing drilling and spotting fluid formulations, since this allows an estimate of the consolidation of the filter cake under the drill string while the string is stuck (for example during a fluid spotting procedure).

Further, it is of advantage to be able to off-centre the probe during the build-up of the filter cake, in order to determine what sort of unbalanced profile would be built up under similar conditions down the well. Lastly, it would be of advantage to be able to determine the filter cake thickness around the entire periphery of the permeable sleeve simulating the rock formation, and over a definite axial length, rather than only in a single location.

GENERAL DESCRIPTION OF THIS INVENTION

Accordingly, this invention provides, for use with an apparatus that includes a main housing, a permeable cylindrical sleeve fixed with respect to the main housing and simulating a rock formation through which a well is drilled, first means defining a compartment exterior to the sleeve, and second means for introducing into the interior of said sleeve a solids-containing fluid and for raising the fluid to a pressure higher than the pressure in said compartment, whereby the fluid passes through the sleeve and into said compartment, leaving a filter cake on the inside of said sleeve; an accessory apparatus comprising a probe adapted to extend through said sleeve and simulate a drill string, third means for moving the probe toward and away from the inside surface of said sleeve, and fourth means for determining the filter cake thickness.

This invention further provides a method of simulating down-hole conditions in a drilled well, comprising the steps: providing an apparatus which includes a main housing, a porous cylindrical sleeve fixed with respect to the main housing and simulating a rock formation through which a well is drilled, first means defining a compartment exterior to the sleeve, second means for introducing into the interior of said sleeve a solids-containing fluid, and for raising said fluid to a pressure higher than the pressure in said compartment, whereby the fluid passes through the sleeve and into said compartment, leaving a filter cake on the inside of said sleeve, and a probe extending through said sleeve and simulating a drill string; and then adjusting the probe toward and away from the inside surface of said sleeve to allow an asymmetric flow of liquid through said sleeve.

A preferred method is one which assesses the stickometric property by bringing the probe into contact with the filter cake and allowing the filter cake to mask a portion of the contact probe from a balance hydrostatic condition, thus developing a differential pressure to cause the probe to stick against the filter cake, then determining the force required to move the probe axially of itself against its stuck condition.

Another possible method involves the provision of a projection on the probe adjacent the sleeve, the projection being brought into contact with the filter cake. This method involves making measurements of the compaction (strain vs. load) in the filter cake.

By providing means to rotate the probe about the central axis of the sleeve, and by providing the probe with an ultrasonic generating and sensing means, it is possible to determine the thickness profile of a filter cake by rotating the probe and simultaneously taking soundings with the ultrasonic device around the periphery of the sleeve, and over a limited axial extent.

By providing an opening in the probe adapted to be closed by the filter cake when the probe contacts the same, and by determining the pressure differential between the opening and the fluid surrounding the probe, filter cake pore pressure can be determined.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figure 1A:
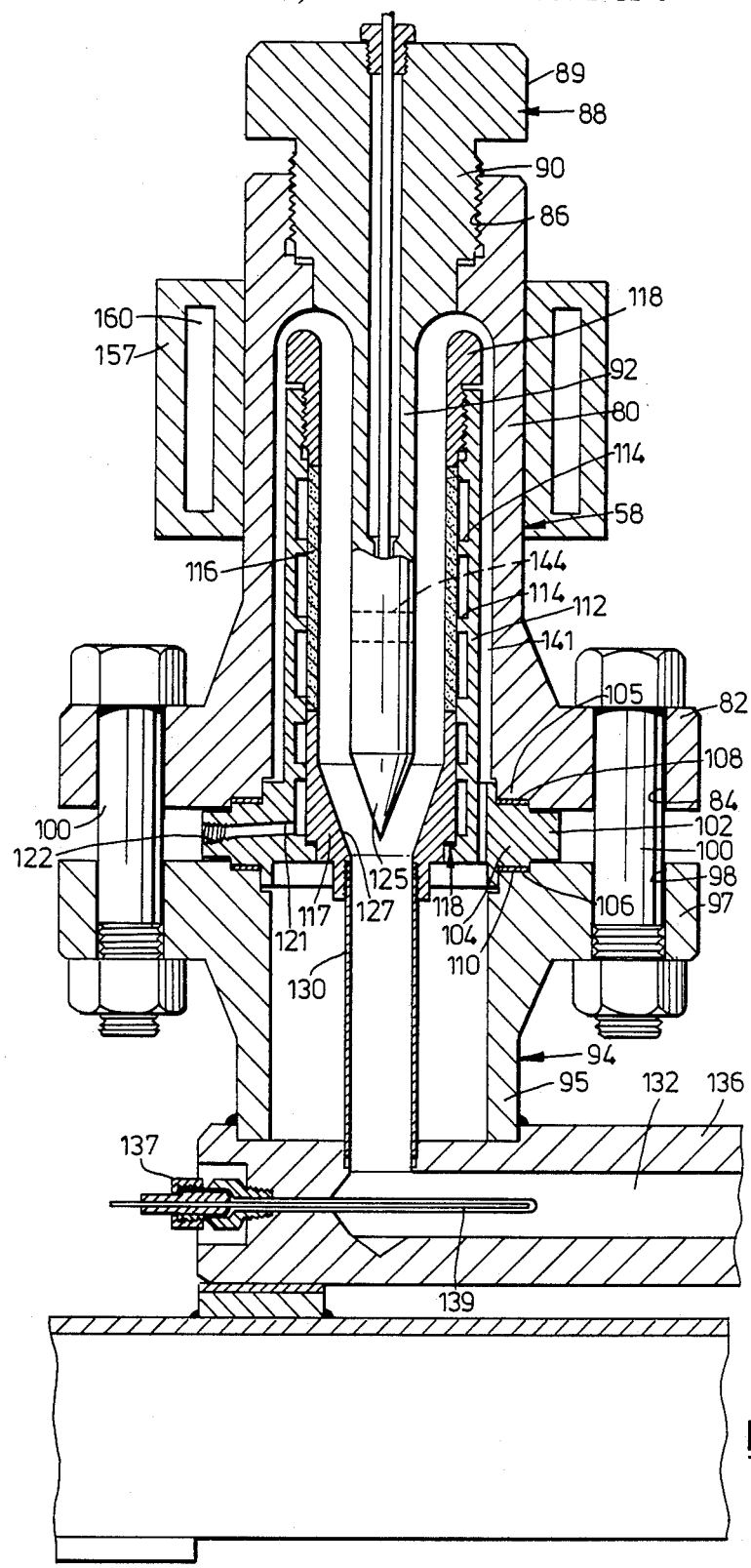
FIG. 1 (broken into 1A and 1B) is a sectional view through a filtration unit, including a circulating pump means, disclosed and claimed in copending U.S. patent application Ser. No. 551,343, filed on Nov. 14, 1983.

Attention is first directed to FIG. 1A, which shows a fluid testing vessel 58 to include a main cylindrical body 80 having a flange 82 for clamping purposes, the flange 82 being provided with a plurality of circumferentially separated bolt holes 84. At the top, the cylindrical member 80 has a threaded bore 86 adapted to receive a plug 88 having a hexagonal top portion 89, a screw-threaded portion 90, and a probe 92, the purpose of which will be explained subsequently. The fluid testing vessel 58 also includes a base member 94 having a downwardly projecting cylindrical portion 95 and a flange 97, the flange having bolt holes 98 corresponding to the bolt holes 84 in the flange 82, such that when the bolt holes are in alignment, a plurality of bolts 100 can be placed therethrough in order to tighten the flanges together. The flanges sandwich between them an insert member 102 having a stepped portion 104 for cooperation with stepped portions 105 and 106 of the cylindrical member 80 and the base member 94, respectively. As can be seen in the figure, annular gaskets 108 and 110 are provided as seals between the various members. The insert 102 includes an upstanding cylindrical portion 112 which comprises inwardly extending ridges 114 adapted to support from the outside a porous, cylindrical sleeve 116 which is sandwiched between an upper plug 118 which has a threaded engagement with the top part of the cylindrical portion 112, and a further insert 117 which has a stepped engagement at 118 with the insert 102. Gaskets are provided at the top and bottom of the cylindrical sleeve 116, these being adapted to cushion the sleeve 116 against excessive loading. It is contemplated that the sleeve 116 be constituted of sintered metal, porous ceramic material, or the like, and it is known that certain of these materials can be very brittle. The cylindrical sleeve 116 could also be machined from a sample of the actual rock being drilled, depending upon the strength of the rock.

The space between the porous cylindrical sleeve 116 and the cylindrical portion 112 of the insert 102 exists by virtue of the spacing provided by the ridges 114. The ridges 114 are not continuous, and therefore the entire volume between the cylindrical sleeve 116 and the cylindrical portion 112 can be considered a single volume. This volume is in communication with an outlet duct 121, which has a pipe-threaded female connecting portion 122, to which a suitable conduit can be connected. The probe 92 extends centrally downwardly within the plug 118, the porous cylindrical sleeve 116, and the upper part of the further insert 117. Furthermore, the probe 92 has a conically tapered lower end 125, in order to facilitate passage of drilling mud around and along the probe 92. Moreover, the further insert 117 has an internal frusto-conical wall 127, again for promoting smooth flow of the drilling mud.

Below the further insert 117, and within the base member 94, a pipe 130 is provided, the pipe 130 connecting with the passage that surrounds the probe 92, and at its lower end connecting with a delivery passageway 132 from a positive displacement pump 134 of known construction. The annular space around the pipe 130 and within the base member 94 constitutes part of a suction passageway for drilling mud, which leads (by a passageway which is not cut by the section shown in FIG. 1A) to the suction side of the positive displacement pump 134. The passageway 132 is defined in a horizontally elongated member 136, into which a mounting means 137 projects a temperature probe 139. The annular passageway between the pipe 130 and the base member 94 connects with a further annular passageway 141 exterior of the cylindrical portion 112 but within the cylindrical member 80, this annular passageway communicating with the top of the passageway between the probe 92 and the porous cylindrical sleeve 116.

Mounted within the probe 92 is an ultrasonic device 144, which includes an ultrasound generator and an ultrasound receiver, capable of determining the mud cake thickness on the inside wall of the porous cylindrical sleeve 116, during operation.

The ultrasonic device is capable of generating an ultrasound signal in the direction radially outwardly from the probe 92, and this signal then is reflected back by caked mud on the porous cylindrical sleeve 116. The length of time taken for the echo to be picked up by the receiver can be used to determine the thickness of the mud cake.

An aluminum block 157 of cylindrical configuration surrounds the cylindrical member 80, and contains within it a conventional heating means, such as a calrod, in the interior 160, this being for the purpose of maintaining the filter cake deposition area at a desired elevated temperature.

Figure 2:
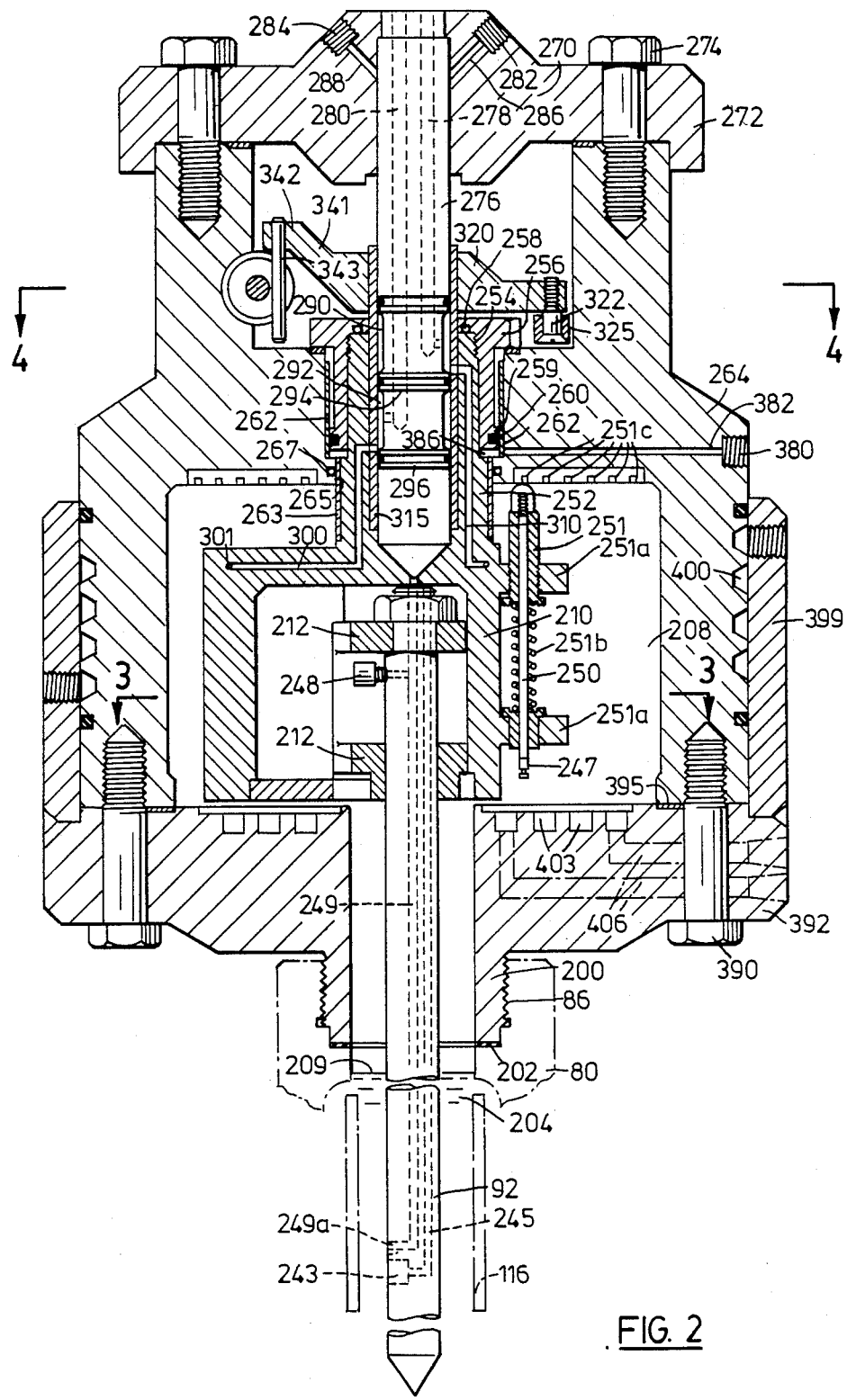
FIG. 2 is an axial sectional view through a apparatus adapted to be affixed to the apparatus shown in FIG. 1, and capable of performing stickometric measurements on a filter cake.

Attention is now directed to FIG. 2, in which the upper portion of the cylindrical member 80 is shown in chain-dotted lines. The internal threads 86 of the member 80 are engaged by a boss 200 which contacts a seal 202 that prevents access to the threads 86 from the annular space surrounding the probe 92. The annular space surrounding the probe 92, shown in FIG. 2 by the numeral 204, has access upwardly to a compartment 208 in which is located a body 210 which may undergo rotation within the compartment 208 and may also move longitudinally in the direction of the axis of the probe 92, by virtue of mechanisms which will be described subsequently. The compartment 208 is filled with nitrogen under pressure, which extends down to the liquid/$N_2$ interface 209.

Figure 4:
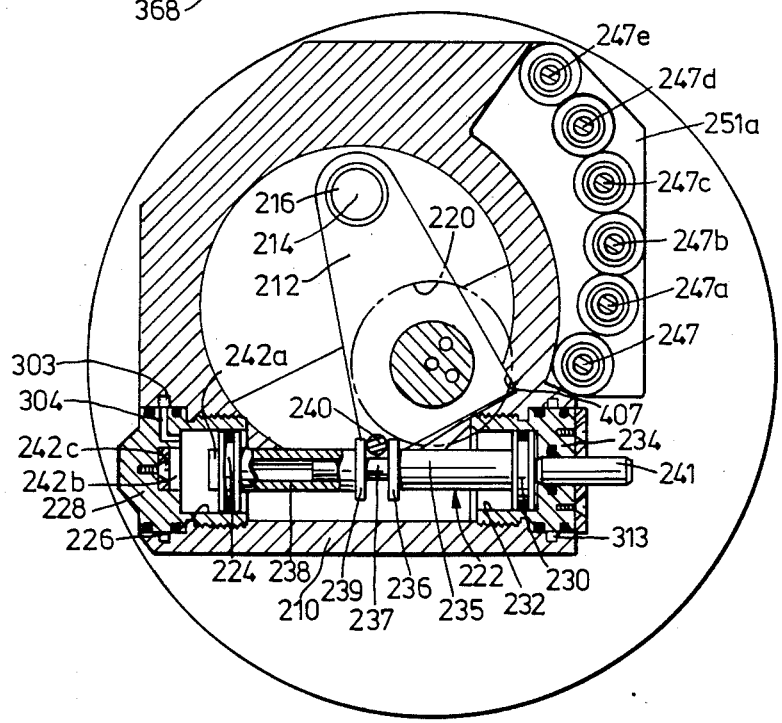
FIG. 4 is a cross-sectional view taken at the line 4—4 in FIG. 2.

As can be seen by looking simultaneously at FIGS. 2 and 4, the upper end of the probe 92 is supported by two axially spaced-apart brackets 212 which are pivoted about an axis identified in FIG. 4 by the numeral 214 and defined by a pin 216 which is journalled with respect to the body 210. As can be particularly well seen in FIG. 4, the brackets 212, which are pivotally mounted with respect to the pin 216, can shift together and carry the probe 92 in an arcuate path toward and away from the wall of the sleeve 116, shown in chain-dotted lines in FIG. 2. The inside surface of the sleeve 116 is identified at 220 in FIG. 4.

Shown in FIG. 4, but not intersected by the section of FIG. 2, is a hydraulically operated composite piston 222 which is double ended, one end 224 sliding in a cylinder 226 defined by a threaded insert 228, the other end 230 sliding in a cylinder 232 defined by an insert 234. The inserts 228 and 234 are threaded into appropriate threaded bores in the body 210. The end 230 is integral with a shaft 235 which has a land 236 and has a smaller-diameter coaxial extension 237. The extension is slidably received in a bore in a shaft 238 integral with the end 224. The shaft 238 has a land 239, and the two lands 236 and 239 capture between them an upstanding rod 240 extending between the two brackets 212. An ultrasonic probe 241 is mounted in the insert 234, the purpose of which is to allow a determination of the position of the piston 222.

The end 224 has affixed thereto a permanent magnet 242a, and a similar magnet 242b is affixed to a machine screw 242c which is screwed into the insert 228.

The probe 92 has mounted therein an ultrasonic generator and receiver shown in broken lines at 243, from which an electrical wire passes upwardly along a vertical bore 245 in the probe 92, and exits at the top thereof, above the uppermost bracket 212. From there, the wire loosely passes to one end of an access bore (not shown) through which it extends to connect to a contact 247 which is mounted to the body 210 and rotates therewith. A pressure transducer 248 is mounted to the probe 92 within the body 210 and communicates along passage 249 with an opening 249a in the side of the probe 92, adjacent the sleeve 116. The transducer 248 is connected via another wire to a contact 247a (see FIG. 4), also secured to rotate with the body 210. The wires have some slack in them to permit the brackets 212 to move the probe 92 toward and away from the interior wall of the sleeve 116.

A plurality of contacts 247–247e are provided, each consisting of a rod 250 sliding within an insulating guide 251 and threaded into a contact 251d. The rod and guide slide within two guide flanges 251a and a spring 251b biases them upwardly into contact with one of a plurality of concentric slip rings 251c. The rod 250 slides within a further insulator guide 251f supported in a bore within the lower guide flange 251a. Electrical connections (not shown) extend from the slip rings 251c to the exterior of the apparatus shown in FIG. 2.

The body 210 is integral with an upstanding boss portion 252, the upper end of which is threaded at 254 into a ratchet wheel member 256. An O-ring seal is provided at 258 between the boss portion 252 and the ratchet wheel member 256.

The ratchet wheel member 256 defines a piston 259 at the bottom, having an O-ring seal 260 which rides against a cylindrical insert 262 internally of a main housing member 264. The insert may typically be of polished bronze.

Below the ratchet wheel member 256, the boss portion 252 has a cylindrical polished sleeve 263, similar to the insert 262, secured thereto. The sleeve 263 is adapted to move axially and radially within a circular opening 265 in the main housing member 264, equipped with an O-ring seal 267.

Extending downwardly from a cap portion 270 which is secured to the main housing member 264 at a flange 272 by virtue of machine bolts 274, is a stationary shaft 276, having two internal bores 278 and 280, each of which communicates with a separate tapped bore 282 and 284, respectively, through drilled passageways 286 and 288, respectively. The drilled bores 282 and 284 are adapted to receive connectors, so that hydraulic lines can be placed into communication with the bores 278 and 280.

As can be seen in FIG. 2, the lower end of the shaft 276 is provided with a first gallery region 290 and a second gallery region 292, these being spaced axially from one another, and separated by a land 294. Below the gallery region 292 is a further land 296, and both of the lands 294 and 296 are provided with an O-ring seal. Similarly, an O-ring seal is provided immediately above the gallery region 290. This allows the definition of two annular compartments, the one being adjacent the gallery region 290, the other being adjacent the gallery region 292. The annular compartment adjacent gallery region 290 is in communication with the bore 278, and the annular compartment adjacent the gallery region 292 is in communication with the bore 280.

In FIG. 2, the body 210 and boss portion 252 are shown in their lowermost position, it being understood that they can rise from that position over a distance permitted by the height of the compartment 208 above the body 210. As seen in FIG. 2, the annular compartment adjacent the gallery region 292 communicates along a passageway 300 with a horizontal passageway 301 which extends in the direction perpendicular to the drawing plane, and which in turn communicates through a vertical passageway (not seen) with an annular gallery 303 surrounding the insert 228 (see FIG. 4). From the gallery 303, a bore 304 communicates with the chamber within the cylinder 226. A similar passageway 310 communicates with the annular compartment adjacent the gallery region 290, and by a like arrangement communicates ultimately with the compartment defined within the cylinder 232, through a gallery 313.

Hence, it will be understood that, regardless of the rotational or vertical orientation of the body 210, the threaded bores 282 and 284 are always in communication with the cylinders 232 and 226, respectively, whereby the position of the piston 222 can be controlled.

It will be seen in FIG. 2 that a cylindrical insert 315 is provided inside the boss portion 252, and runs in contact with the O-ring seals in the lands 294 and 296, as well as the O-ring seal above the gallery region 290.

Mounted for rotation about the central axis of the shaft 276, and riding against the cylindrical insert 315 is a pawl arm 320, which supports a stub shaft 322 from which a pawl 325 is pivoted. The pawl 325 is spring biased so that its operative end 326 seeks to engage the teeth 327 of the ratchet wheel member 256. The main housing 264 pivotally supports a further pawl 334 which turns about a threaded pin 336 that is fixed with respect to the main housing member 264. The pawl 334 has a contact end 339 which likewise contacts the teeth 327 of the ratchet wheel member 256, due to the fact that the pawl 334 is spring biased in the clockwise sense (spring not shown).

As can be seen in FIG. 2, the pawl arm 320 undergoes an oblique upward step at 341 and terminates in an elevated portion 342 from which downwardly extends a pin 343.

Figure 3:
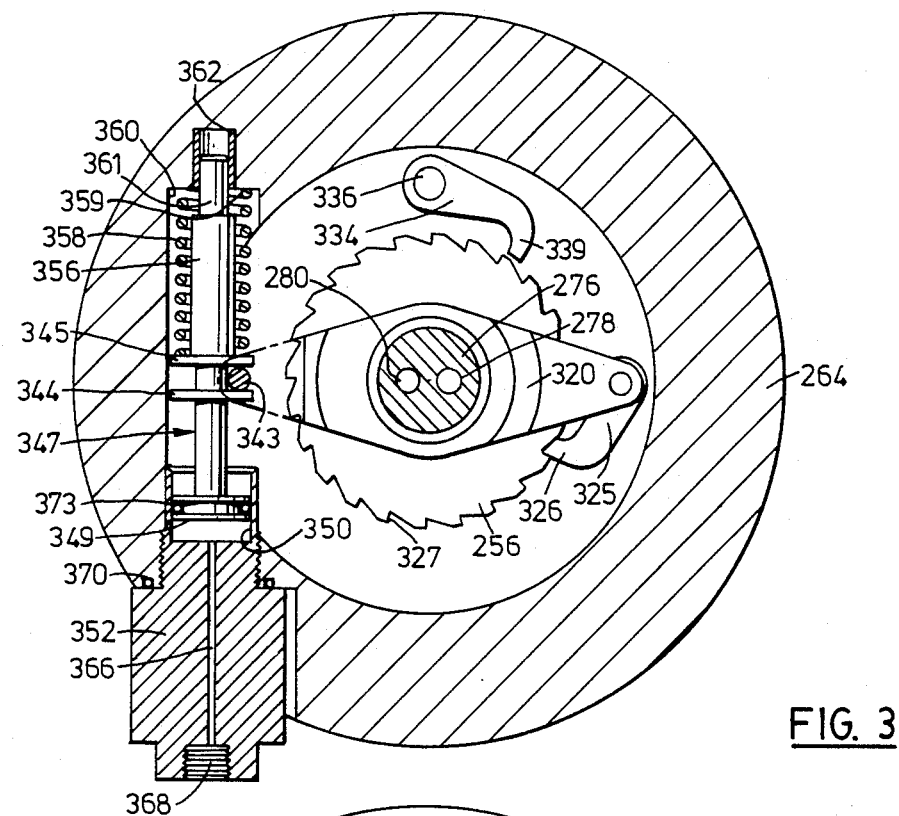
FIG. 3 is a cross-sectional view taken at the line 4—4 in FIG. 2.

As now seen in FIG. 3, the pin 343 is captured between two lands 344 and 345 of a hydraulically operated piston 347 having one end 349 riding within a cylinder 350 defined by a threaded insert 352, and having the other end 356 shaped to receive one end of a compression spring 358, of which the other end bears against the end wall 359 of a cylindrical recess 360. The end 356 of the piston 347 has a reduced extension 361 slidably engaging a sleeve 362 in a continuation of the recess 360. A passageway 366 communicates the chamber defined by the cylinder 350 with a threaded bore 368. An O-ring seal 370 is provided for the insert 352, and the portion 349 of the piston 347 is also provided with an O-ring seal 373.

It will be appreciated that, by pressurizing the compartment defined by the cylinder 350, the hydraulically-operated cylinder 347 can be caused to move upwardly in FIG. 3 against the urging of the compression spring 358, thus rotating the pawl arm 320 in the clockwise sense as seen in FIG. 3, thus causing the pawl 325 to urge the ratchet wheel member 356 also in the clockwise sense. When an angular movement the equivalent of one tooth has been undergone, the other pawl 334 will lodge behind the tooth and prevent return motion of the ratchet wheel member, so that the pawl arm 320 can return to the original position and allow the pawl 325 to lodge behind the next tooth. By sending repeated pulses to the chamber defined by the cylinder 350, the ratchet wheel member 356, and thus the body 210, can be rotated to any desired position in a rotational sense.

In order to raise the body 210 upwardly, hydraulic pressure is admitted through a threaded bore 380, along a passageway 382, and into a compartment 386 below the ratchet wheel member 256, and in particular below the piston 259 defined at the bottom of the ratchet wheel member 256. Gravity is used to allow the body 210 to descend.

Machine bolts 390 secure a flange 392 integral with the boss 200 to the main housing member 264, with the provision of a circular seal 395 to seal the compartment 208. The flange 392 is secured to an upstanding shell 399 which defines a spiral cooling passage 400 with the main housing member 264, into which the appropriately shaped groove is machined.

Similarly, a spiral passage seen in section at 403 in FIG. 2 allows for additional temperature control, through passageways identified generally by the numeral 406. This provision allows a significantly lower temperature in compartment 208 than in the test fluid.

The attachment apparatus described with reference to FIGS. 2, 3 and 4 may be utilized for a number of different functions, as follows.

Figure 1B:
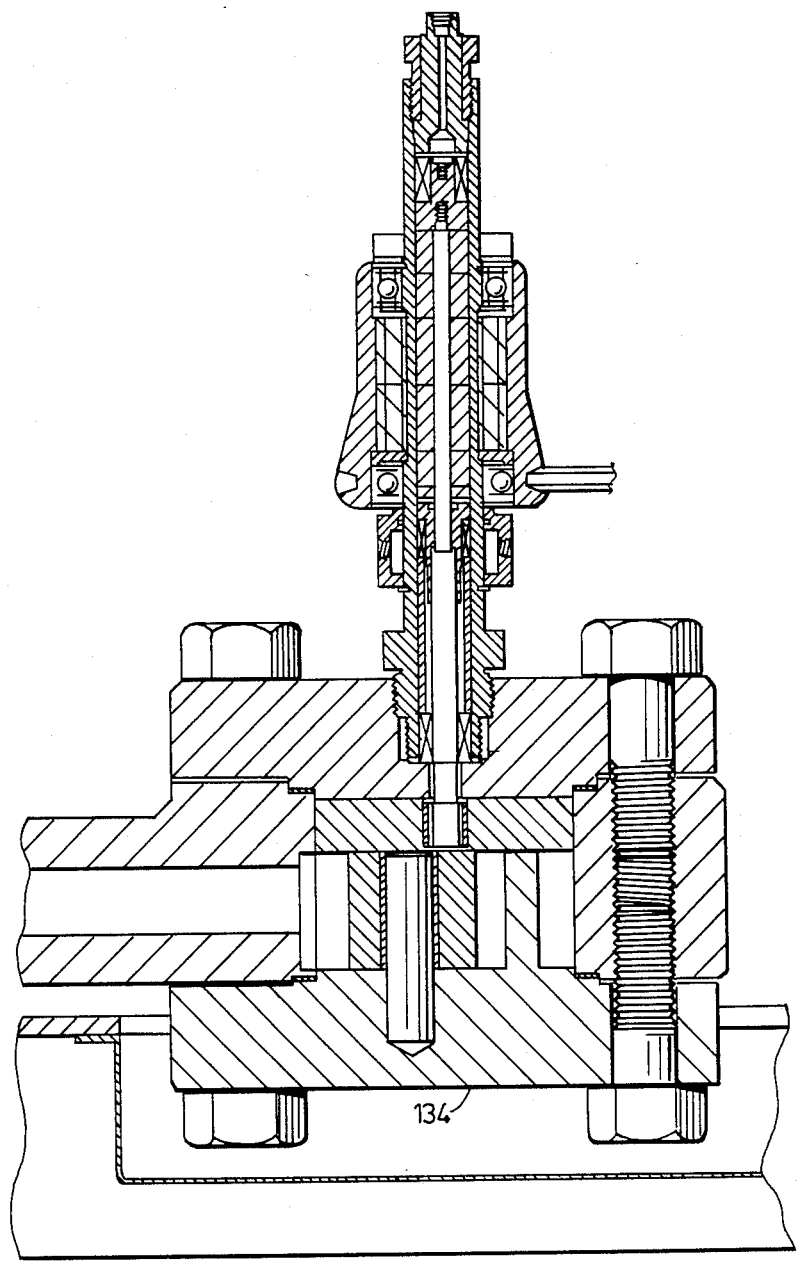

Firstly, in order to simulate an off-centre drill string down a well-bore, it is merely necessary to move the probe 92 to an intermediate position between the axially centred position shown in FIG. 2 and a position in which it is in contact with the interior surface of the sleeve 116. Then, the apparatus shown in FIG. 1 is placed into operation in order to cause a filter cake to be deposited on the inside surface of the sleeve 116. Because of the off-centre positioning of the probe 92, it will be appreciated that the flow rates of the fluid toward and through the sleeve 116 will be different for different peripheral locations around the sleeve. This in turn will cause variable deposition and erosion rates for the filter cake.

It will be appreciated that the piston 222 can be moved to the left in FIG. 4 by admitting pressurized fluid along passageway 310 to the chamber within bore 232 to the right of the end 230. This urges the probe 92 leftwardly to assume an off-centre position. If the probe 92 is not in contact with the interior wall of the sleeve 116, the slidable relation between the shafts 235 and 238 will permit leftward drifting of the probe, should a differential pressure arise due to differing flow rates around its periphery. If the probe 92 should seek to approach the closer side of the sleeve 116, the leftward piston end 224 could be moved back to the right to establish a stop or limit to this approach.

When it is desired to allow differential pressure on the probe 92 to move it against the filter cake, the piston 222 is used to bring the probe to a close approach, at which point the magnets 224 and 224b attract each other and withdraw the land 239 out of interfering relation with the probe, thus leaving it free to move leftwardly. This arrangement is utilized when seeking to test the stickometric properties of the filter cake, since the removal of the land 236 out of the way prevents it from interfering with encroachment of the probe 92 into the filter cake, regardless of where the rightward end 230 of the piston 222 is located at the time.

It will be appreciated that, in the arrangement shown in FIG. 4, the piston 224 is capable of locking the probe 92 in a centred position with respect to the interior surface 220 of the sleeve 116, by virtue of the fact that the brackets 212 lodge at their rightward corners against a stop 407 which is machined into the interior of the body 210. In FIG. 4 the components are shown in the position in which the probe 92 is in this blocked condition.

In order to determine the filter cake profile around the periphery of the sleeve 116, the apparatus of FIG. 2 is operated first to return the probe 92 to its centred position with respect to the sleeve 116, and then the ratchet apparatus at the top of the body 210 (shown in section in FIG. 3) is operated to progressively rotate the probe about its centre axis (coaxial with the sleeve 116), while the ultrasonic device 243 takes soundings by echoing an ultrasound pulse from the surface of the filter cake deposited on the inside surface of the sleeve 116. A suitable electronic apparatus (not shown) can be employed to interpret the electronic signals thus generated, and (if desired) display the resultant filter cake profile on a screen.

It will be appreciated that the profile of the filter cake can be taken at more than a single horizontal level, due to the ability of the probe to be raised.

If it is desired to test the stickometric properties of a filter cake, the filter cake is first deposited in the normal way, typically with the probe 92 on centre with respect to the sleeve 116. Then, the piston 222 is activated by applying hydraulic pressure within the chamber defined by the cylinder 232, to move the piston 222 to the left as seen in FIG. 4, thus bringing the land 237 into contact with the rod 240, thus rotating the brackets 212 in the clockwise sense about the axis 214 and carrying the probe 92 toward the interior wall of the sleeve 116. It will be appreciated, from an inspection of FIG. 4, that the probe 92 will approach the interior surface of the sleeve 116 substantially normally, partly due to the substantial length of the swing arm from the pivot axis 214 to the probe 92. From the ultrasonic sounding previously taken, an accurate idea may be had as to the specific location of the surface of the filter cake. The piston 222 is moved just far enough to bring the probe 92 into the vicinity of contact with the filter cake, but does not force the probe into the filter cake. Because the land 239 is magnetically withdrawn to the left, the entire force causing the probe 92 to enter the filter cake arises due to the differential pressure between the interior of the sleeve 116 and the cavity which surrounds the sleeve 116. This differential pressure will cause the probe to be urged tightly into the filter cake, and it will become stuck in this position to a greater or lesser degree, depending upon the characteristics of the filter cake itself. Consolidometric properties of the filter cake can be determined by taking measurements at time intervals of the encroachment of the probe into the filter cake.

In order to test the force necessary to release the probe 92 from its stuck position with respect to the filter cake, hydraulic pressure is applied through the passageway 382 to a location below the piston 259 defined at the bottom of the ratchet wheel member 256. The pressure is gradually increased until the probe moves, and in this manner the threshold force required can be determined.

In order to determine the threshold force just mentioned, the pressure of the hydraulic fluid in passageway 382 is monitored, and it will be found that there is a spike in the pressure at the point when movement begins. This pressure spike will indicate the hydraulic pressure just prior to breaking the probe free of the filter cake, and from that pressure the force seeking to lift the probe at the point of release can be calculated.

To determine the filter pore pressure where the same is contacted by the probe 92, the reading provided by the transducer 248 is monitored as the probe 92 encroaches into the filter cake. The opening 249a is located on the mid-line of contact between the probe 92 and the filter cake.

In the appended claims, the word "fluid" is used to include the drilling mud or other test material of which certain properties can be determined by the apparatus and method herein disclosed. It is also conceivable that a foam material could be utilized in place of the drilling mud, the foam thus not being a liquid strictly speaking. It is for this reason that the term "fluid" is believed more appropriate in the claims.

While one embodiment of this invention has been illustrated in the accompanying drawings and described in the foregoing disclosure, it will be apparent to those skilled in the art that changes and modifications may be made therein without departing from the essence of the invention, as set forth in the appended claims.

The embodiments of the invention in which an exclusive property or privilege is claimed are defined as follows:

1. An apparatus, comprising:
   a main housing,
   a permeable cylindrical sleeve fixed with respect to the main housing and simulating a rock formation through which a well is drilled,
   first means defining a compartment exterior to the sleeve,
   second means for introducing into the interior of said sleeve a solids-containing fluid, and for pressurizing the fluid to a pressure higher than the pressure in said compartment, whereby some of the fluid passes radially through the sleeve and into said compartment due to a pressure differential across said sleeve, leaving a filter cake on the inside of said sleeve,
   a rod-like, elongated probe extending through said sleeve and simulating a drill string,
   third means for moving the probe toward and away from the inside surface of said sleeve while said second means is operating to create said pressure differential across the sleeve,
   and fourth means for determining the filter cake thickness.

2. The apparatus claimed in claim 1, in which the fourth means includes ultrasonic means mounted to said probe, adapted to direct an ultrasound signal toward said filter cake and to receive the echo back.

3. The apparatus claimed in claim 2, in which the third means further includes rotary means for selectively rotating the probe.

4. The apparatus claimed in claim 3, in which the rotary means rotates the probe about the axis of the sleeve.

5. The apparatus claimed in claim 1, in which said second means is also adapted to cause the fluid to flow axially through the sleeve as the filter cake is being deposited.

6. The apparatus claimed in claim 1 in which the probe is cylindrical, has a tapering free end, and is supported at the other end by two brackets spaced-apart longitudinally of the probe and pivoted about an axis spaced from but parallel to the axis of the probe, said third means including a hydraulically operated piston member having means for moving said brackets about their pivot axis.

7. The apparatus claimed in claim 6, in which the pivot axis of said brackets is fixed with respect to a body forming part of rotary means for selectively rotating the probe about the axis of the sleeve, the said body being fixed with respect to a ratchet wheel adapted to coact with pawl means that rotate the ratchet wheel, and thus the body, and thus the probe.

8. The apparatus claimed in claim 7, in which the pawl means includes a pawl arm pivoted about the ratchet wheel axis, the latter being the same as the sleeve axis, a first pawl pivoted to the pawl arm spaced from the pawl arm pivot, and a second pawl pivoted with respect to said main housing, both pawls engaging said ratchet wheel, and a hydraulically operated piston for oscillating the pawl arm with respect to the main housing.

9. The apparatus claimed in claim 1, having fifth means for moving the probe axially of itself and for determining the force required to do so.

10. The apparatus claimed in claim 9, in which said fifth means includes hydraulic piston means.

11. A method of simulating down-hole conditions in a drilled well, comprising the steps:

providing a main housing and a permeable cylindrical sleeve fixed with respect to the main housing and simulating a rock formation through which a well is drilled, together with first means defining a compartment exterior to the sleeve and second means for introducing into the interior of the sleeve a solids-containing fluid, and for increasing the fluid pressure in the sleeve above that in said compartment, whereby some of the fluid passes radially through the sleeve and into said compartment due to a pressure differential across the sleeve, leaving a filter cake on the inside of the sleeve, a rod-like, elongated probe extending through the sleeve and simulating a drill string, and adjusting the probe toward and away from the inside surface of said sleeve to allow an asymmetric flow of fluid through said sleeve, while simultaneously passing fluid radially outwardly through the sleeve and into the compartment.

12. A method of determining the thickness profile of a filter cake, comprising the steps:

providing a main housing, a permeable cylindrical sleeve fixed with respect to the main housing and simulating a rock formation through which a well is drilled, first means defining a compartment exterior to the sleeve, second means for introducing into the interior of said sleeve a solids-containing fluid, and for raising the fluid to a pressure higher than the pressure in said compartment, whereby the fluid passes through the sleeve and into said compartment, leaving a filter cake on the inside of said sleeve, a probe extending through said sleeve and simulating a drill string, the probe being movable toward and away from the inside surface of the sleeve, positioning the probe at a desired location within the sleeve and introducing the solids-containing fluid into the interior of said sleeve in order to deposit a filter cake on the inside of the sleeve, then positioning the probe in the axial centre of the sleeve, then rotating the probe about the sleeve axis while measuring the filter cake thickness by means of an ultrasonic generating and receiving means mounted in the probe adjacent the sleeve.

13. The method claimed in claim 12, in which the probe is then changed to a different axial position while still in the axial centre of the sleeve, then rotated about the sleeve axis while measuring the filter cake thickness, whereby a further filter cake profile at a different horizontal level may be obtained.

14. A method of making stickometric measurements of a filter cake under simulated down-hole conditions for a drilled well, comprising the steps:

providing a main housing, a permeable cylindrical sleeve fixed with respect to the main housing and simulating a rock formation through which a well is drilled, a first means defining a compartment exterior to the sleeve, second means for introducing into the interior of said sleeve a solids-containing fluid and for raising the fluid in the sleeve to a pressure higher than the pressure in said compartment, whereby some of the fluid passes radially through the sleeve and into said compartment due to a pressure differential across the sleeve, leaving a filter cake on the inside of said sleeve, a rod-like, elongated probe extending through said sleeve and simulating a drill string, moving the probe toward the inside surface of said sleeve to bring it into contact with the filter cake while simultaneously passing fluid radially outwardly through the sleeve and into the compartment, thereby masking the probe from a balanced hydrostatic condition, whereby the imbalance tends to drive the probe further into the filter cake, then causing the probe to move axially of itself and determining the threshold force at which the probe begins to move against the filter cake.

15. A method of making stickometric measurements of a filter cake under simulated down-hole conditions for a drilled well, comprising the steps:

providing a main housing, a permeable cylindrical sleeve fixed with respect to the main housing and simulating a rock formation through which a well is drilled, first means defining a compartment exterior to the sleeve, second means for introducing into the interior of said sleeve a solids-containing fluid, and for raising the fluid in the sleeve to a pressure higher than the pressure in said compartment, whereby some of the fluid passes radially through the sleeve and into said compartment due to a pressure differential across the sleeve, leaving a filter cake on the inside of said sleeve, and a rod-like, elongated probe extending through said sleeve and simulating a drill string, moving the probe toward the inside surface of said sleeve to bring it into contact with the filter cake while simultaneously passing fluid radially outwardly through the sleeve and into the compartment, and urging the probe into the filter cake by the application of an external load on the probe, then causing the probe to move axially of itself and determining the threshold force at which the probe begins to move against the filter cake.

16. A method of determining consolidometric properties of a filter cake under down-hole conditions simulating a drilled well, comprising the steps:

providing a main housing, a permeable cylindrical sleeve fixed with respect to the main housing and simulating a rock formation through which a well is drilled, first means defining a compartment exterior to the sleeve, second means for introducing into the interior of said sleeve a solids-containing fluid, and for raising the fluid in the sleeve to a pressure higher than the pressure in said compartment, whereby some of the fluid passes radially through the sleeve and into said compartment due to a pressure differential across the sleeve, leaving a filter cake on the inside of said sleeve, and a rod-like, elongated probe extending through said sleeve and simulating a drill string, moving the probe toward the inside surface of the sleeve to bring it into contact with a filter cake formed as a result of fluid passing through the sleeve, while simultaneously passing fluid radially outwardly through the sleeve and into the compartment, allowing differential pressure to cause encroachment of the probe into the filter cake, and taking measurements at time intervals of the encroachment of the probe into the filter cake.

17. A method of determining the pore pressure in a filter cake under down-hole conditions simulating a drilled well, comprising the steps:

providing a main housing, a permeable cylindrical sleeve fixed with respect to the main housing and simulating a rock formation through which a well is drilled, first means defining a compartment exterior to the sleeve, second means for introducing into the interior of said sleeve a solids-containing fluid, and for raising the fluid to a pressure higher than the pressure in said compartment, whereby the fluid passes through the sleeve and into said compartment, leaving a filter cake on the inside of said sleeve, and a probe extending through said sleeve and simulating a drill string, the probe having an opening in its side, the opening being in communication with means for determining the pressure differential between the opening and a medium in which the probe is immersed, moving the probe toward the inside surface of the sleeve to bring it into contact with a filter cake formed as a result of fluid passing through the sleeve, the said opening being at the location of contact between the probe and the filter cake, and determining the differential pressure between the opening and the interior of the sleeve.

18. The method claimed in claim 17, in which the opening is located on the contact centre line of the probe with respect to the filter cake.

19. The apparatus claimed in claim 1, further incorporating an opening in the side of the probe, the opening communicating internally of the probe with means for determining the pressure differential between the opening and the interior of the sleeve.

20. For use with an apparatus which includes a main housing, a permeable cylindrical sleeve fixed with respect to the main housing and simulating a rock formation through which a well is drilled, first means defining a compartment exterior to the sleeve, and second means for introducing a solids-containing fluid into the interior of said sleeve, and for pressurizing the fluid in the sleeve to a pressure higher than the pressure in said compartment, whereby some of the fluid passes radially through the sleeve and into said compartment due to a pressure differential across said sleeve, leaving a filter cake on the inside of said sleeve, an accessory apparatus comprising:

a rod-like, elongated probe adapted to extend through said sleeve and simulate a drill string, third means for moving the probe toward and away from the inside surface of the sleeve, while said second means is operating to create said pressure differential across said sleeve, and fourth means for determining the filter cake thickness.

21. The apparatus claimed in claim 20, in which the fourth means includes ultrasonic means mounted to said probe, adapted to direct an ultrasound signal toward said filter cake and to receive the echo back.

22. The apparatus claimed in claim 21, in which the fourth means further includes rotary means for selectively rotating the probe.

23. The apparatus claimed in claim 22, in which the rotary means rotates the probe about the axis of the sleeve.

24. The apparatus claimed in claim 20, in which said second means is also adapted to cause the fluid to flow axially through the sleeve as the filter cake is being deposited.

25. The apparatus claimed in claim 20 in which the probe is cylindrical, has a tapering free end, and is supported at the other end by two brackets spaced-apart longitudinally of the probe and pivoted about an axis spaced from but parallel to the axis of the probe, said third means including a hydraulically operated piston member having means for moving said brackets about their pivot axis.

26. The apparatus claimed in claim 25, in which the pivot axis of said brackets is fixed with respect to a body forming part of rotary means for selectively rotating the probe about the axis of the sleeve, the said body being fixed with respect to a ratchet wheel adapted to coact with pawl means that rotate the ratchet wheel, and thus the body, and thus the probe.

27. The apparatus claimed in claim 26, in which the pawl means includes a pawl arm pivoted about the ratchet wheel axis, the latter being the same as the sleeve axis, a first pawl pivoted to the pawl arm spaced from the pawl arm pivot, and a second pawl pivoted with respect to said main housing, both pawls engaging said ratchet wheel, and a hydraulically operated piston for oscillating the pawl arm with respect to the main housing.

28. The apparatus claimed in claim 20, having fifth means for moving the probe axially of itself and for determining the force required to do so.

29. The apparatus claimed in claim 28, in which said fifth means includes hydraulic piston means.

30. The method claimed in claim 11, in which the adjustment of the probe occurs while simultaneously flowing fluid axially through the sleeve.

31. The method claimed in claim 14, in which, while the probe is moved toward said inside surface, and subsequently is moved axially of itself, fluid is being caused to flow axially through the sleeve.

32. The method claimed in claim 15, in which, while the probe is moved toward said inside surface, and subsequently is moved axially of itself, fluid is being caused to flow axially through the sleeve.

33. The method claimed in claim 16, in which, while the probe is moved toward said inside surface, fluid is being caused to flow axially through the sleeve.

* * * * *